(12) United States Patent
Selker et al.

(10) Patent No.: US 10,893,832 B2
(45) Date of Patent: Jan. 19, 2021

(54) PREDICTIVE INSTRUMENT TO IDENTIFY PATIENTS FOR USE OF PHARMACOLOGICAL CARDIAC METABOLIC SUPPORT

(71) Applicant: Tufts Medical Center, Inc., Boston, MA (US)

(72) Inventors: Harry P. Selker, Wellesley, MA (US); Madhab Ray, Andover, MA (US)

(73) Assignee: Tufts Medical Center, Inc., Boston, MA (US)

( * ) Notice: Subject to any disclaimer, the term of this patent is extended or adjusted under 35 U.S.C. 154(b) by 852 days.

(21) Appl. No.: 15/404,646

(22) Filed: Jan. 12, 2017

(65) Prior Publication Data

US 2017/0196505 A1 Jul. 13, 2017

Related U.S. Application Data

(60) Provisional application No. 62/278,002, filed on Jan. 13, 2016.

(51) Int. Cl.
*A61B 5/00* (2006.01)
*A61B 5/021* (2006.01)
*A61B 5/0452* (2006.01)
*G16H 15/00* (2018.01)

(52) U.S. Cl.
CPC ............ *A61B 5/4848* (2013.01); *A61B 5/021* (2013.01); *A61B 5/0452* (2013.01); *A61B 5/7275* (2013.01); *G16H 15/00* (2018.01)

(58) Field of Classification Search
CPC ..... A61B 5/4848; A61B 5/7275; A61B 5/021; A61B 5/0452; G16H 15/00
See application file for complete search history.

(56) References Cited

U.S. PATENT DOCUMENTS

| | | | | |
|---|---|---|---|---|
| 8,548,778 B1* | 10/2013 | Hart | ........................ | G06T 19/20 703/6 |
| 9,087,147 B1* | 7/2015 | Fonte | .................... | A61B 5/7275 |
| 2003/0187362 A1* | 10/2003 | Murphy | ................ | G06T 7/0012 600/508 |
| 2005/0171503 A1* | 8/2005 | Van Den Berghe | ......................... | A61M 5/1723 604/504 |
| 2009/0036364 A1* | 2/2009 | Levy | .................... | C07K 14/575 514/1.1 |
| 2012/0065514 A1* | 3/2012 | Naghavi | ................ | G16H 50/20 600/454 |
| 2014/0288085 A1* | 9/2014 | Yadav | .................. | A61K 31/519 514/250 |
| 2014/0371610 A1* | 12/2014 | Liu | ....................... | A61B 5/7267 600/509 |
| 2015/0066818 A1* | 3/2015 | Choi | .................. | A61B 5/02007 706/12 |

* cited by examiner

*Primary Examiner* — Gary Jackson
*Assistant Examiner* — Sebastian X Lukjan
(74) *Attorney, Agent, or Firm* — Occhiuti & Rohlicek LLP

(57) ABSTRACT

A purpose-made predictive instrument for the administration of cardiac metabolic support for acute coronary syndromes (ACS, which include unstable angina and acute myocardial infarction) that particularly identifies those most likely to benefit from treatment. In some examples, such a predictive instrument is used for real-time decision support for the administration of treatments such as glucoseinsulin-potassium (GIK).

9 Claims, 2 Drawing Sheets

PREDICTIVE INSTRUMENT TO IDENTIFY PATIENTS FOR USE OF PHARMACOLOGICAL CARDIAC METABOLIC SUPPORT

CROSS REFERENCE TO RELATED APPLICATIONS

This application claims the benefit of the filing date of U.S. Provisional Application No. 62/278,002, filed on Jan. 13, 2016, the contents of which are hereby incorporated by reference in the entirety.

BACKGROUND

This invention relates to a predictive instrument used to identify patients for use of pharmacological cardiac metabolic support.

In general, a number of prior uses of predictive instruments have focused on using information associated with a specific patient (e.g., derived from clinical and electrocardiogram measurements) to provide an output indicative of a diagnosis. One such output is a probability of a particular medical condition, such as a probability of cardiac ischemia. Other prior uses of predictive instruments have focused on prediction of the patient's future clinical outcomes, such as a probability of death within 30 days, or a probability of cardiac arrest within the next two days. One prior approach, referred to as the "Acute Cardiac Ischemia Time-Insensitive Predictive Instrument" (ACI-TIPI) uses electrocardiograph-based measurements and provides a clinician (e.g., an emergency physicians or paramedic) with predictions of the probability of a given patient having acute cardiac ischemia, also known as acute coronary syndromes (ACS, which included unstable angina and acute myocardial infarction). The 0-100% probability of ACS augments the clinician's judgment in triage of the patient. This output is typically used in much the same way as a published probability of rain in a weather report may supplement a person's decision of whether to carry an umbrella. It is not completely clear how the clinicians make use of the probability in practice, and whether different clinicians make use of the output in a consistent and unbiased manner.

More specifically, a number of prior patents and patent applications of an inventor of the present patent application relate to the approaches outlined above. For example, U.S. Pat. No. 4,957,115, "Device for Determining the Probability of Death of Cardiac Patients" addresses prediction of whether a patient will die, without consideration of the treatment options. As another example, U.S. Pat. No. 5,276,612 "Risk Management System for use with Cardiac Patients," addresses the question of whether a patient has a particular heart condition. U.S. Pat. No. 6,067,446, "Diagnostic Tool using a Predictive Instrument," similarly focuses in estimating a probability of a medical outcome or diagnosis. U.S. Pat. No. 4,998,535, "Thrombolysis Predictive Instrument," describes an approach to prediction of the clinical outcomes from using thrombolytic therapy to treat a patient with a heart condition. This method involves separately predicting a probability of death with and without using the therapy. US Pat. Pub. 2004/0045560, "Computer-Assisted Multi-Dimensional Patient Selection," describes a similar approach directed to using a predictive instrument to indicate whether to administer thrombolytic therapy by predicting two probabilities of a good outcome, one under the assumption that the therapy is administered and one under the probability that it is not.

SUMMARY

In one aspect, in general, a purpose-made predictive instrument for the administration of cardiac metabolic support for acute coronary syndromes (ACS, which include unstable angina and acute myocardial infarction) that specifically identifies those most likely to receive a net benefit from treatment. In some examples, such a predictive instrument is used for real-time decision support for the administration of treatments such as intravenous glucose-insulin-potassium (GIK) solution.

One advantage of such a predictive instrument is that it can be a companion diagnostic to a specific set of one or more metabolic support drugs, such as GIK. The combination of the predictive instrument and the specific set of support drugs can undergo trials and their use validated in combination.

Other features and advantages of the invention are apparent from the following description, and from the claims.

DESCRIPTION

In a first embodiment described below, which is referred to as a "Cardiac Metabolic Support Predictive Instrument" (CMSPI), focuses directly on an outcome, and more particularly, on the relative benefit of administering a particular therapy as compared to not administering the therapy. For example, an instance of a CMSPI is associated with the specific metabolic support drug GIK. An output of the CMSPI provides a measure of an expected benefit of administering the specific drug. A goal is to identify those patients who would most likely benefit and/or those patients who would benefit to a greatest degree. For example, it may be that there are complex factors such that a patient that will benefit the most must both have a high probability of ACS, and also have other characteristics that would make that patient a good candidate for treatment with GIK. Prior approaches may address the first part—a high probability of ACS, but the assessment of the degree of benefit for a given patient, thereby informing the clinician as to he or she being a good candidate for the particular drug is provided by this new approach.

This embodiment relies on an analysis phase in which information associated with past patients, at least some of whom received GIK, is used to determine configuration data that is used to assess the information for a new patient in a prediction phase. In general, this configuration data is used in a computation that processes the information for the new patient to provide the output, which indicates whether the patient is benefit from the administration of GIK. In at least some versions of this embodiment, the configuration data and processor that performed the computation is embedded in an electrocardiograph device, with at least some of the information associated with the new patient being derived from the signals acquired from the patient by the electrocardiogram device.

The computation that provides the output indicative of whether the patient will benefit from the administration of GIK may make use of a variety of mathematical underpinnings. As one example, and as outlined in more detail below, logistic regression may be used. However, it should be understood that logistic regression, or the particular form of logistic regression outlined below, are only examples, and other types of mathematical or non-mathematical (e.g., heuristic, machine intelligence, expert system, and/or statistical) approaches may be used in alternative embodiments.

A variety of information about a patient may be used in different versions. In some versions, the information includes a combination of one or more of the following:
  Blood pressure
  Electrocardiographic (ECG) ST elevation
  Other ECG changes
  Time duration from onset of symptoms In a number of embodiments, the information may be represented as a numerical vector, referred to as X.

Figure 1:
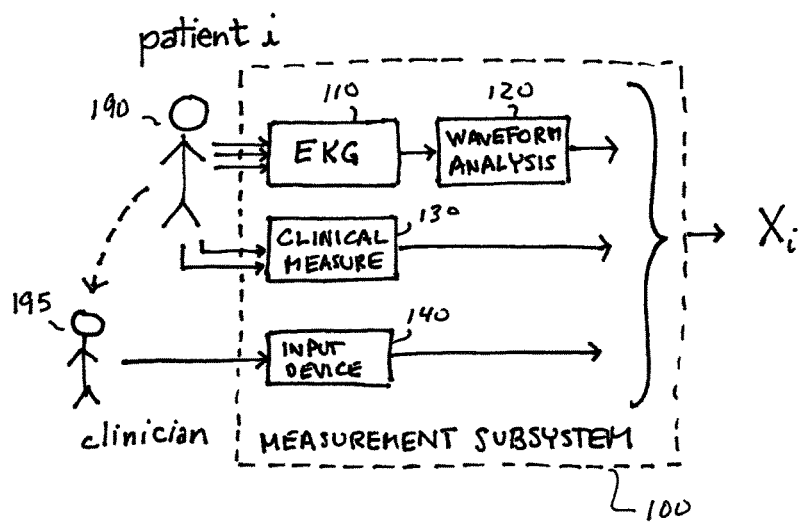
FIG. 1 is a block diagram showing a measurement system.

Referring to FIG. 1, a measurement subsystem 100 is used to acquire information $X_i$ about a patient i (190). As introduced above, some of the information is determined by use of an electrocardiograph 110, which produces waveforms representing the patient's heart function. These waveforms are processed by a waveform analysis component 120, which produces numerical (or in some embodiments categorical) characterizations of the waveforms. The subsystem 100 also includes other clinical measurement components 130, for example, providing direct measurements of quantities such as blood pressure. A clinician 195, who observes (and optionally interacts with) the patient 190 also provides information via an input device 140. For example, indication of the patient's sex, the time duration from the onset of symptoms etc. may be provided via the input device 140. As illustrated, information $X_i$ is them assembled using a combination (e.g., concatenation) of the information from the various sources.

Figure 2:
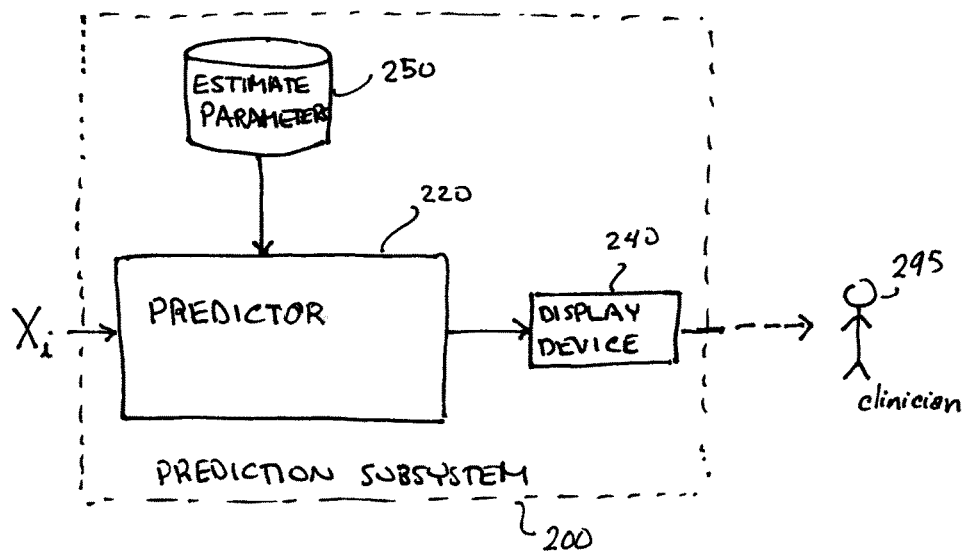
FIG. 2 is a block diagram showing a prediction system.

Referring to FIG. 2, a prediction subsystem 200 is used to process the information $X_i$ about a patient to provide an output indicative of whether the patient will benefit from the administration of the therapy. As discussed more fully below, a predictor 220, which may be implemented as a mathematical computation, uses estimated parameters 250 to determine the output, which is passed to a display device 240 for presentation to a clinician 295 (e.g., the same clinician 195 who provided information about the patient, or in some embodiments, the clinician 295 is different than the clinician 195).

A variety of quantifications of benefit may be used. In some versions, the data for past patients in the analysis phase includes a binary indicator, for example, that indicates whether the patient exhibited a specific outcome, for example, that the patient died or suffered cardiac arrest within a fixed period (e.g., 30 days) from when the information for the patient was gathered. In a number of embodiments, the outcome may be represented as a binary variable y, which takes on a value 1 if the specific outcome is observed and 0 otherwise. Note that an outcome may be a composite of a number of different clinical conditions, for example, the logical union of death within one time duration and a heart attack within a second shorter duration.

The output essentially relates a prediction of the future for the patient under the two scenarios: for example, administration of GIK and non-administration of GIK. In a number of embodiments, whether or not the drug was administered is represented by a variable z, which takes on the value 1 if the drug was administered and a value 0 if it was not. One possible, but not necessarily a best choice, is to present two quantitative: the probability of the specified outcome with administration (Prob(outcome|administration), which can be represented as P(y=1|X,z=1)); and the probability of the specified outcome without administration (Prob(outcome|non-administration), which can be represented as P(y=1|X,z=0)). Assuming the outcome is undesireable (e.g., death or cardiac arrest), another choice of output is a reduction in probability of the outcome (e.g., Prob(outcome|non-administration)−Prob(outcome|administration), which can be represented as P(y=1|X,z=0)−P(y=1|X,z=1)), the inverse of this difference, sometimes referred to as the "Number Needed to Treat" (NNT), or a ratio of the probabilities (e.g., Prob(outcome|non-administration)/Prob(outcome|administration), which can be represented as P(y=1|X,z=0)/P(y=1|X,z=1)).

In a number of implementations of the data analysis phase, the available data includes a set of past patients, only some of whom had the drug administered (i.e., z=1), and only some of who exhibited the specified outcome (i.e., y=1). In general, each of the patients is associated with information X for that patient (although in some implementations, it is possible that some patients have incomplete information yet can nevertheless contribute in the data analysis phase). Therefore, the data for analysis may be represented as a data set of items $(X_i, y_i, z_i)$ for i=1, . . . , N, where N is the number of past patients in the data set.

Figure 3:
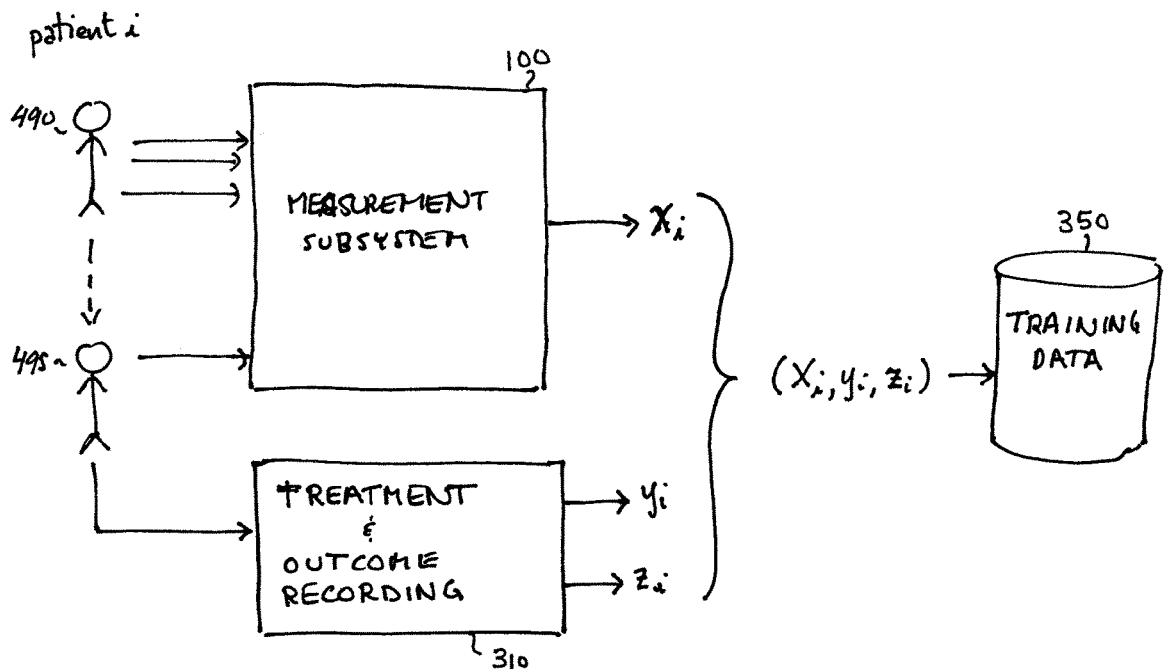
FIG. 3 is a block diagram that illustrates a data collection system.

Referring to FIG. 3, collection of data about past patients 490 makes use of the measurement subsystem 100 (or a functionally equivalent system) and also have a component for recording the treatment ($z_i$) and the outcome ($y_i$), which are provided by a person 495 via an input device. The data for a set of past ("training") patients 490 is collected in a training data set 350, for example, stored in a database.

Figure 4:
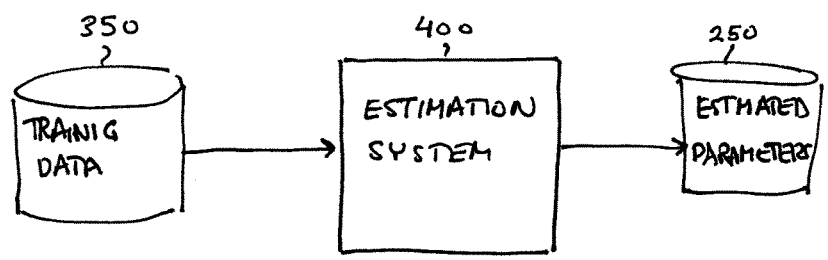
FIG. 4 is a block diagram showing an estimation system.

Referring to FIG. 4, generally, an estimation system 400 processes the training data set 350 to produce the estimated parameters 250, which are used by the predictor as illustrated in FIG. 2. Possible implementations of the predictor 220 of FIG. 2 and corresponding estimation system 400 of FIG. 4 are discussed below.

One possible approach to implementing the analysis phase is used the estimation system 400 to determine a set of numerical parameters, α and β, which together form the estimated parameters 250, such that the probability of the outcome is modeled as $$\hat{P}(y=1 \mid X, z) = \frac{e^{\alpha + \gamma z + \beta X}}{1 + e^{\alpha + \gamma z + \beta X}}$$

where $\hat{P}(y=1|X,z)$ is the estimate of the probability of the specified outcome for a patient with information vector X, and indicator z of whether the drug was administered. A number of well-known approaches to determining the parameters α and β can be used, for example, based on Logistic Regression techniques.

Figure 5:
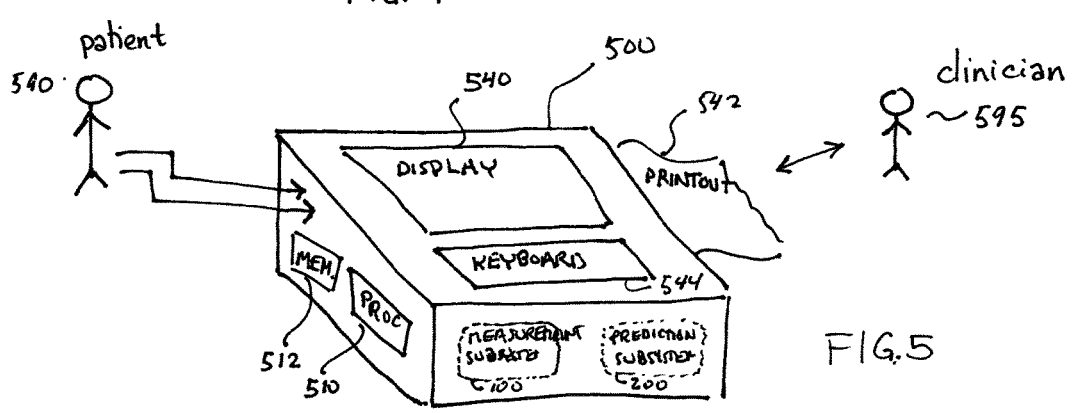
FIG. 5 is an illustration of an embodiment of a system that incorporates a measurement system and a prediction system.

Referring to FIG. 5, an implementation of a runtime system 500 is integrated with an electrocardiogram device. The system 500 includes a processor 510 and memory 520. The memory 520 includes storage of the estimated parameters 250, while the processor 510 along with parts of the memory 520 implement the functionality of the measurement subsystem 100 and prediction subsystem 200. The system 500 includes a display 540 and produces a printout 542, which together provide a way of communicating the output to a clinician 595 (e.g., one of clinician 295 shown above). The system 500 includes a keyboard 544, or other input device, through which the clinician 595 (serving the function of the clinician 195 of FIG. 1).

In an embodiment that makes use of Logistic Regression as discussed above, when a new patient 590 is considered, the information vector X for that patient is determined, and one of the quantities described above representing the benefit of administering the drug is computed. For example, a Number Needed to Treat (NNT) quantity (recognizing that the smaller NNT is, the more likely the benefit) is computed as $$\hat{N}NT(X) = (\hat{P}(y=1 \mid X, z=1) - \hat{P}(y=1 \mid X, z=0))^{-1} =$$
$$\left(\frac{e^{\alpha+\gamma+\beta X}}{1+e^{\alpha+\gamma+\beta X}} - \frac{e^{\alpha+\beta X}}{1+e^{\alpha+\beta X}}\right)^{-1}$$

This quantity is then displayed to the clinician 595, who uses the information in deciding whether to administer the therapy, for example, whether to administer GIK.

Between the analysis phase for determining the estimated parameters, and the runtime phase when a new patient is considered, a clinical trial phase may be conducted to validate the safety and effectiveness of a clinician following the indicated output from the predictor. In the trial, the estimated parameters are fixed and are associated with a specific therapy, such as administration of a specific dosage of GIK. After the clinical trial has validated the combination of the predictor (and implicitly the measurement subsystem, and a decision rule, such as administer if NNT<20) and the drug as two components of a therapy, that combination may receive approval from the appropriate governing organizations (e.g., the United States Food and Drug Administration). In this way the approval is not associated with the predictor or with the drug individually, but is associated with the combination of the predictor (and its measurement subsystem and decision rule) and the drug.

Implementations of certain components (e.g., the predictor 220 and the associated estimation system 400) may be implemented in hardware and/or in software using stored instructions for causing a processor, such as a processor embedded in an electrocardiogram device, to perform the functions of those components as described above. Such software may be stored in a non-transient memory device, such as in a semiconductor memory.

It is to be understood that the foregoing description is intended to illustrate and not to limit the scope of the invention, which is defined by the scope of the appended claims. Other embodiments are within the scope of the following claims.

What is claimed is:

1. A method for determining whether to administer a metabolic support agent to a patient, the method comprising:
    accessing stored data that includes a plurality of estimated parameters characterizing a relationship between a relative benefit for the patient of administering the metabolic support agent versus not administering said agent, said parameters having been determined by an analysis of data for a plurality of prior individuals, said data including for each individual from the plurality of prior individuals (a) a plurality of measured features of said each individual from the plurality of prior individuals, (b) an indicator associated with whether the metabolic agent was administered to said each individual from the plurality of prior individuals, and (c) an indicator of an outcome for said each individual from the plurality of prior individuals, wherein the benefit is defined in terms of the predicted outcome for the patient;
    measuring a plurality of features of the patient;
    processing the measured plurality of features using a predictive instrument configured according to the accessed data for the plurality of prior individuals to determine the expected benefit of administering the metabolic support agent;
    providing an output to a clinician characterizing the determined expected benefit,
    wherein processing the measured plurality of features using the predictive instrument comprises computing the expected benefit based on an inverse of a difference between a first probability, derived according to the parameters determined from the accessed data for the plurality of prior individuals, of achieving a specific outcome if the metabolic support agent is administered to the patient, and a second probability, derived from the parameters determined according to the accessed data for the plurality of prior individuals, of achieving the specific outcome if the metabolic support agent is not administered to the patient.

2. The method of claim 1 wherein the metabolic support agent comprises glucoseinsulin-potassium (GIK).

3. The method of claim 1 further comprising determining whether the patient is exhibiting an acute coronary syndrome (ACS).

4. The method of claim 1 further comprising determining the data including the estimated parameters, including analyzing the data of the plurality of prior individuals.

5. The method of claim 4 wherein determining the data including the estimated parameters includes performing a logistic regression using the data of the plurality of prior individuals.

6. A clinical support device comprising:
    a data storage device including a section for storing a plurality of estimated parameters characterizing a relationship between a relative benefit for the patient of administering the metabolic support agent versus not administering said agent, said parameters having been determined by an analysis of data for a plurality of prior individuals, said data including for each individual from the plurality of prior individuals (a) a plurality of measured features of said each individual from the plurality of prior individuals, (b) an indicator associated with whether the metabolic agent was administered to said each individual from the plurality of prior individuals, and (c) an indicator of an outcome for said each individual from the plurality of prior individuals, wherein the benefit is defined in terms of the predicted outcome for the patient;
    a measurement subsystem for measuring a plurality of features of the patient;
    a prediction subsystem, coupled to the data storage device and to the measurement subsystem for processing the measured plurality of features using a predictive instrument configured according to the accessed data for the plurality of prior individuals to determine the expected benefit of administering the metabolic support agent;
    wherein processing the measured plurality of features using the predictive instrument comprises computing the expected benefit based on an inverse of a difference between a first probability, derived according to the parameters determined from the accessed data for the plurality of prior individuals, of achieving a specific outcome if the metabolic support agent is administered to the patient, and a second probability, derived from the parameters determined according to the accessed data for the plurality of prior individuals, of achieving the specific outcome if the metabolic support agent is not administered to the patient; and an output device for providing an output to a clinician characterizing the determined expected benefit.

7. The clinical support device of claim 6 wherein the measurement subsystem includes an electrocardiogram and a waveform analysis component coupled to the electrocardiogram for determining as least some features of the plurality of features of the patient.

8. The clinical support device of claim 6 wherein the metabolic support agent comprises glucoseinsulin-potassium (GIK).

9. The method of claim 1, wherein the specific outcome comprises a composite of a plurality of possible clinical outcomes for the patient.

\* \* \* \* \*